United States Patent [19]

Georg et al.

[11] Patent Number: 5,972,668
[45] Date of Patent: Oct. 26, 1999

[54] PRODUCTION OF MULTI-ENZYME GRANULES

[75] Inventors: Meine Georg, Mettman; Karl-Heinz Maurer, Erkrath; Albrecht Weiss, Langenfeld; Kathleen Paatz, Duesseldorf; Ulrich Haas, Erkrath; Monika Boecker, Leichlingen, all of Germany

[73] Assignee: Henkel Kommanditgesellschaft auf Aktien, Duesseldorf, Germany

[21] Appl. No.: 08/765,379

[22] PCT Filed: Jun. 19, 1995

[86] PCT No.: PCT/EP95/02363

§ 371 Date: Jul. 3, 1997

§ 102(e) Date: Jul. 3, 1997

[87] PCT Pub. No.: WO96/00773

PCT Pub. Date: Jan. 11, 1996

[30] Foreign Application Priority Data

Jun. 28, 1994 [DE] Germany .................. 44 22 433

[51] Int. Cl.⁶ .................. C12N 9/96; C11D 7/42; C11D 17/04; C11D 3/386
[52] U.S. Cl. .................. 435/188; 510/284; 510/393; 510/530
[58] Field of Search .................. 510/284, 393, 510/530; 435/188

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,703,798 | 3/1955 | Schwartz | 260/211 |
| 3,547,828 | 12/1970 | Mansfield et al. | 252/351 |
| 3,632,957 | 1/1972 | Hannah | 219/119 |
| 3,737,376 | 6/1973 | Ziffer | 195/63 |
| 3,784,476 | 1/1974 | van Kampen et al. | 252/109 |
| 4,106,991 | 8/1978 | Markussen et al. | 195/63 |
| 4,264,738 | 4/1981 | Stepanov et al. | 435/222 |
| 4,266,031 | 5/1981 | Tang et al. | 435/188 |
| 4,287,082 | 9/1981 | Tolfo et al. | 252/174.12 |
| 4,372,868 | 2/1983 | Saran et al. | 252/102 |
| 4,404,115 | 9/1983 | Tai | 252/135 |
| 4,435,307 | 3/1984 | Barbesgaard et al. | 252/174.12 |
| 4,443,355 | 4/1984 | Murata et al. | 252/174.12 |
| 4,462,922 | 7/1984 | Boskamp | 252/174.12 |
| 4,566,985 | 1/1986 | Bruno et al. | 134/42 |
| 4,585,642 | 4/1986 | Rieck | 423/333 |
| 4,590,237 | 5/1986 | Wuhrmann et al. | 524/480 |
| 4,636,468 | 1/1987 | Arbige et al. | 435/198 |
| 4,664,839 | 5/1987 | Rieck | 252/175 |
| 4,665,029 | 5/1987 | Iwai et al. | 435/198 |
| 4,702,857 | 10/1987 | Gosselink | 252/174.12 |
| 4,713,194 | 12/1987 | Gosselink | 252/174.23 |
| 4,726,954 | 2/1988 | Arbige et al. | 426/35 |
| 4,751,003 | 6/1988 | Raehse et al. | 210/639 |
| 4,810,414 | 3/1989 | Huge-Jensen et al. | 252/174.12 |
| 4,813,552 | 3/1989 | Walter | 211/105.1 |
| 4,820,439 | 4/1989 | Rieck | 252/175 |

(List continued on next page.)

FOREIGN PATENT DOCUMENTS

| | | |
|---|---|---|
| 814956 | 6/1969 | Canada . |
| 923069 | 3/1973 | Canada . |
| 958618 | 12/1974 | Canada . |
| 974907 | 9/1975 | Canada . |
| 989557 | 5/1976 | Canada . |
| 1036455 | 8/1978 | Canada . |
| 1338237 | 4/1996 | Canada . |
| 006638 | 1/1980 | European Pat. Off. . |
| 28865 | 5/1981 | European Pat. Off. . |
| 037026 | 10/1981 | European Pat. Off. . |
| 066944 | 12/1982 | European Pat. Off. . |
| 080223 | 6/1983 | European Pat. Off. . |
| 080748 | 6/1983 | European Pat. Off. . |
| 92355 | 10/1983 | European Pat. Off. . |
| 117553 | 9/1984 | European Pat. Off. . |
| 130064 | 1/1985 | European Pat. Off. . |
| 150386 | 8/1985 | European Pat. Off. . |
| 164514 | 12/1985 | European Pat. Off. . |
| 164552 | 12/1985 | European Pat. Off. . |
| 167309 | 1/1986 | European Pat. Off. . |
| 168526 | 1/1986 | European Pat. Off. . |
| 185427 | 6/1986 | European Pat. Off. . |
| 200032 | 11/1986 | European Pat. Off. . |
| 204284 | 12/1986 | European Pat. Off. . |
| 214761 | 3/1987 | European Pat. Off. . |
| 241984 | 10/1987 | European Pat. Off. . |
| 258068 | 3/1988 | European Pat. Off. . |
| 262588 | 4/1988 | European Pat. Off. . |
| 265832 | 5/1988 | European Pat. Off. . |
| 269977 | 6/1988 | European Pat. Off. . |
| 270974 | 6/1988 | European Pat. Off. . |
| 273125 | 7/1988 | European Pat. Off. . |
| 293753 | 12/1988 | European Pat. Off. . |
| 301298 | 2/1989 | European Pat. Off. . |
| 301414 | 2/1989 | European Pat. Off. . |
| 304332 | 2/1989 | European Pat. Off. . |
| 305216 | 3/1989 | European Pat. Off. . |
| 309931 | 4/1989 | European Pat. Off. . |
| 330641 | 8/1989 | European Pat. Off. . |
| 331376 | 9/1989 | European Pat. Off. . |
| 334462 | 9/1989 | European Pat. Off. . |
| 339550 | 11/1989 | European Pat. Off. . |
| 341947 | 11/1989 | European Pat. Off. . |
| 357969 | 3/1990 | European Pat. Off. . |
| 362671 | 4/1990 | European Pat. Off. . |
| 375102 | 6/1990 | European Pat. Off. . |
| 376705 | 7/1990 | European Pat. Off. . |
| 378261 | 7/1990 | European Pat. Off. . |
| 378262 | 7/1990 | European Pat. Off. . |
| 384717 | 8/1990 | European Pat. Off. . |
| 385401 | 9/1990 | European Pat. Off. . |

(List continued on next page.)

Primary Examiner—Jon P. Weber
Attorney, Agent, or Firm—Ernest G. Szoke; Wayne C. Jaeschke; Henry E. Millson, Jr.

[57] ABSTRACT

A process is presented for producing stable multi-enzyme containing granules. The process involves the steps of mixing a reversible competitive inhibitor with a first enzyme, adding a second incompatible enzyme, adding a carrier, extruding and granulating the resulting mixture and reducing the moisture content if necessary.

24 Claims, No Drawings

U.S. PATENT DOCUMENTS

| | | | |
|---|---|---|---|
| 4,832,866 | 5/1989 | Schulz et al. | 252/321 |
| 4,865,774 | 9/1989 | Fabry et al. | 252/554 |
| 4,876,024 | 10/1989 | Enomoto et al. | 252/174.12 |
| 4,904,599 | 2/1990 | Ozaki et al. | 435/252.33 |
| 4,933,287 | 6/1990 | Farin et al. | 435/198 |
| 4,943,532 | 7/1990 | Kawai et al. | 435/209 |
| 4,945,053 | 7/1990 | Ito et al. | 435/209 |
| 4,950,417 | 8/1990 | Bycroft et al. | 252/174.12 |
| 4,962,030 | 10/1990 | Kawai et al. | 435/209 |
| 4,966,996 | 10/1990 | Schäfer | 562/598 |
| 5,002,695 | 3/1991 | Schulz et al. | 252/321 |
| 5,039,446 | 8/1991 | Estell | 510/321 |
| 5,093,256 | 3/1992 | Shen et al. | 435/198 |
| 5,100,796 | 3/1992 | Paridans et al. | 435/198 |
| 5,108,457 | 4/1992 | Poulose et al. | 8/111 |
| 5,138,046 | 8/1992 | Wuest et al. | 536/18.6 |
| 5,153,135 | 10/1992 | Farin et al. | 435/253.3 |
| 5,166,069 | 11/1992 | Shen et al. | 435/252.5 |
| 5,183,651 | 2/1993 | Schimmel et al. | 423/334 |
| 5,229,095 | 7/1993 | Schimmel et al. | 423/334 |
| 5,240,851 | 8/1993 | Paridans et al. | 435/253.3 |
| 5,268,156 | 12/1993 | Schimmel et al. | 423/334 |
| 5,275,753 | 1/1994 | de Buzzaccarini et al. | 252/95 |
| 5,278,066 | 1/1994 | Andreoli et al. | 435/252.34 |
| 5,290,694 | 3/1994 | Nakanishi et al. | 435/198 |
| 5,308,596 | 5/1994 | Kotzian et al. | 423/333 |
| 5,318,733 | 6/1994 | Carduck et al. | 264/15 |
| 5,352,604 | 10/1994 | Wilson et al. | 435/221 |
| 5,356,607 | 10/1994 | Just | 423/334 |
| 5,374,716 | 12/1994 | Biemann et al. | 536/18.6 |
| 5,382,377 | 1/1995 | Raehse et al. | 252/174 |
| 5,417,951 | 5/1995 | Just | 423/334 |
| 5,422,030 | 6/1995 | Panandiker et al. | 252/135 |
| 5,427,936 | 6/1995 | Moeller et al. | 435/198 |
| 5,431,842 | 7/1995 | Panandiker et al. | 510/321 |
| 5,442,100 | 8/1995 | Bjorkquist et al. | 562/7 |
| 5,472,628 | 12/1995 | Panandiker et al. | 510/300 |
| 5,476,608 | 12/1995 | Boyer et al. | 252/135 |
| 5,527,487 | 6/1996 | Mikkelsen et al. | 510/393 |
| 5,529,917 | 6/1996 | Andreoli et al. | 435/198 |
| 5,541,316 | 7/1996 | Engelskirchen et al. | 510/471 |
| 5,674,833 | 10/1997 | Mikkelsen et al. | 510/530 |
| 5,789,364 | 8/1998 | Sell et al. | 510/284 |
| 5,846,798 | 12/1998 | Paatz et al. | 435/187 |

FOREIGN PATENT DOCUMENTS

| | | |
|---|---|---|
| 425427 | 5/1991 | European Pat. Off. . |
| 436835 | 7/1991 | European Pat. Off. . |
| 451921 | 10/1991 | European Pat. Off. . |
| 452428 | 10/1991 | European Pat. Off. . |
| 468102 | 1/1992 | European Pat. Off. . |
| 218272 | 3/1992 | European Pat. Off. . |
| 502325 | 9/1992 | European Pat. Off. . |
| 511456 | 11/1992 | European Pat. Off. . |
| 548599 | 6/1993 | European Pat. Off. . |
| 583536 | 2/1994 | European Pat. Off. . |
| 1803099 | 5/1969 | Germany . |
| 1617188 | 2/1971 | Germany . |
| 1617190 | 2/1971 | Germany . |
| 1940488 | 2/1971 | Germany . |
| 2044161 | 4/1971 | Germany . |
| 1767568 | 7/1971 | Germany . |
| 2101803 | 7/1971 | Germany . |
| 2030531 | 12/1971 | Germany . |
| 2032768 | 1/1972 | Germany . |
| 2137042 | 2/1972 | Germany . |
| 2137043 | 2/1972 | Germany . |
| 1617141 | 4/1972 | Germany . |
| 2121397 | 11/1972 | Germany . |
| 2253063 | 5/1973 | Germany . |
| 2200911 | 10/1973 | Germany . |
| 2412837 | 10/1974 | Germany . |
| 2730481 | 1/1978 | Germany . |
| 2925427 | 1/1981 | Germany . |
| 1617232 | 2/1982 | Germany . |
| 3117250 | 4/1982 | Germany . |
| 3207825 | 9/1982 | Germany . |
| 3207847 | 9/1982 | Germany . |
| 3322950 | 1/1984 | Germany . |
| 3436194 | 4/1986 | Germany . |
| 255884 | 4/1988 | Germany . |
| 4041752 | 6/1992 | Germany . |
| 4221381 | 2/1994 | Germany . |
| 4300772 | 7/1994 | Germany . |
| 4329463 | 3/1995 | Germany . |
| 04238809 | 8/1992 | Japan . |
| 04260610 | 9/1992 | Japan . |
| 1362365 | 8/1974 | United Kingdom . |
| WO 90/09440 | 8/1990 | WIPO . |
| WO 90/10695 | 9/1990 | WIPO . |
| WO 90/13533 | 11/1990 | WIPO . |
| WO 91/02047 | 2/1991 | WIPO . |
| WO 91/02792 | 3/1991 | WIPO . |
| WO 91/08171 | 6/1991 | WIPO . |
| WO 91/16422 | 10/1991 | WIPO . |
| WO 92/06984 | 4/1992 | WIPO . |
| WO 92/11347 | 7/1992 | WIPO . |
| WO 93/11215 | 6/1993 | WIPO . |
| WO 93/16110 | 8/1993 | WIPO . |

PRODUCTION OF MULTI-ENZYME GRANULES

BACKGROUND OF THE INVENTION

1. Field of the Invention

This invention relates to enzyme granules containing at least two different enzymes, to a process for their production and to the use of the granules in solid or liquid detergents and cleaning formulations.

2. Statement of Related Art

Enzymes, especially proteases, are widely used in detergents, washing aids and cleaning products. Normally, the enzymes are not used as pure substances, but rather in the form of mixtures with a diluent/carrier material. If enzyme preparations of this type are added to conventional detergents, a considerable reduction in enzyme activity can occur during storage, especially if bleaching-active compounds are present. Application of the enzymes to carrier salts and simultaneous granulation in accordance with DE-OS 16 17 190 or by bonding using nonionic surfactants in accordance with DE-OS 16 17 188 or aqueous solutions of cellulose ethers in accordance with DE-OS 17 67 568 does not lead to a significant improvement in storage stability because the sensitive enzymes are generally situated on the surface of the carrier in mixtures of the type in question. Although the stability of the enzymes in storage can be significantly increased by coating the enzymes with or encapsulating them in the carrier material and converting them into the required particle form by extrusion, pressing and spheronizing, as described for example in DE-PS 16 17 232, in DE-OS 20 32 768 and in DE-ASS 21 37 042 and 21 37 043, corresponding enzyme preparations have poor solubility properties. The undissolved particles can become caught up in and thus soil the washing or pass into the wastewater without being used. Although the encapsulating compositions known from DE-OS 18 03 099, which consist of a mixture of solid acids or acidic salts and carbonates or bicarbonates and which disintegrate on addition of water, improve the solubility of the enzyme preparations, they are extremely sensitive to moisture and, accordingly, require additional protective measures. Another disadvantage of the above-mentioned preparation is that the enzymes can only be processed in the form of dry powders. The fermenter broths typically accumulating in the enzyme production process cannot be used in this form, but have to be freed from water beforehand.

EP 168 526 describes enzyme granules which contain water-swellable starch, zeolite and a water-soluble granulation aid. This document proposes a production process for such formulations which overcomes the problem mentioned above and which essentially comprises concentrating a fermenter solution freed from insoluble constituents, introducing the additives mentioned and granulating the resulting mixture. The process using the additive mixture proposed therein is advantageously carried out with fermentation solutions which have been concentrated to a relatively high dry matter content, for example of 55% by weight.

International patent application WO 92/11347 describes enzyme granules for use in granular detergents and cleaning compositions which contain 2% by weight to 20% by weight of enzyme, 10% by weight to 50% by weight of swellable starch, 5% by weight to 50% by weight of water-soluble organic polymer as granulation aid, 10% by weight to 35% by weight of cereal flour and 3% by weight to 12% by weight of water. These additives enable the enzyme to be processed without significant losses of activity. In addition, the storage stability of the enzymes in the granules is also satisfactory.

As demonstrated by way of example by the documents cited above, a broad prior art exists in the field of the production of granular enzyme preparations, so that various possibilities for making up individual enzymes in particulate form are available to the expert. Unfortunately, the methods mentioned fail when two or more enzymes capable of reacting with one another are to be incorporated in the same granule. This problem arises in particular in connection with protease which, as a protein-degrading enzyme, is of course capable of decomposing a second enzyme and/or other enzyme present at the same time. If this decomposition process takes place during the production and/or storage of the enzyme granules, the effect of the second enzyme and/or other enzymes under in-use conditions is no longer guaranteed.

Solutions to this problem have also been proposed in the prior art. Thus, according to International patent application WO 90/09440, two-enzyme granules are produced by coating a protease- and cellulose-containing core with a total of 10 layers (alternately stearic acid/palmitic acid glyceride and kaolin) the quantity of protective coating material in the Examples exceeding the quantity of core, subsequently applying a mixture of a second enzyme, a binder, a filler and a granulation aid and, finally, applying an outer coating. A production process such as this is unfavorable on account of the large amount of separating material required between the enzyme-containing core and the layer containing the second enzyme which lies further to the outside. Another disadvantage can be that, under in-use conditions, the enzyme on the outside dissolves first, the second enzyme only being released from the core at a later stage so that the two enzymes are unable to develop their effects at the same time.

Hitherto unpublished German patent application DE 43 29 463 describes a process for the production of multi-enzyme granules in which two separately prepared batches of granules differing in size and each containing an enzyme are agglomerated in a subsequent co-granulation step.

It is known from European patent application EP 304 332 that enzyme-containing basic granules can be coated with powder-form components containing a second enzyme. However, this method of producing multi-enzyme granules often leads to inadequate stability of the second enzyme present in the outer layer which, in addition, has to be prepared beforehand in powder form—another disadvantage of this method. In this variant, too, the two enzymes are generally not released simultaneously in the wash or cleaning liquor.

DESCRIPTION OF THE INVENTION

Accordingly, the problem addressed by the present invention was to provide a simple process for producing particulate enzyme preparations containing at least two different enzymes reacting with one another which would enable the enzymes to be incorporated in the multi-enzyme granules without any loss of activity and to remain therein in storage-stable manner. Surprisingly, this problem has been essentially solved by the use of a competitively reversibly inhibited enzyme in the form of an aqueous formulation which is mixed with more enzyme and additives and extruded in the form of this mixture.

Accordingly, the present invention relates a process for the production of enzyme granules containing at least two different enzymes by mixing an aqueous liquid containing a first enzyme, which may optionally be a fermentation broth freed from insoluble constituents and concentrated, with a competitive inhibitor for this enzyme, subsequently mixing the primary enzyme with the second enzyme or with further enzymes, incorporating an organic and/or inorganic carrier material, extruding the resulting mixture of enzymes and additives through a multiple-bore die followed by a cutting unit, optionally spheronizing the extrudate in a spheronizing unit and drying and, if desired, applying an optionally dye- and/or pigment-containing coating.

The present invention also relates to the use of the multi-enzyme granules obtainable in this way in detergents or cleaning compositions, more especially in particulate detergents or cleaning compositions.

The process according to the invention provides enzyme granules which are suitable for incorporation in detergents and cleaning formulations and which are characterized in that they contain at least two different enzymes, more particularly enzymes which are capable of reacting with one another, i.e. which are not compatible with one another, in homogeneous distribution. The enzymes incompatible with one another may be incorporated together by the process according to the invention in granules in which they are present in substantially homogeneous form, but do not adversely affect one another. A crucial requirement in this regard is that the secondary enzyme should not be directly added to the concentrated aqueous primary enzyme solution, instead the primary enzyme should first be reversibly inactivated by a competitive inhibitor in the aqueous concentrate. Under in-use conditions, i.e. in water-containing wash or cleaning liquors, the inhibition of the primary enzyme is eliminated by the disintegration of the granule structure and by the dissolution of the inhibitor so that the primary and secondary enzymes develop their effects at more or less the same time. The primary enzyme is preferably protease while the secondary enzyme is preferably amylase, lipase, cellulase, hemicellulase, oxidase, peroxidase or mixtures thereof. The secondary enzyme may be incorporated in the primary enzyme in liquid form, for example as a commercial concentrate, or in solid made-up form, for example in the form of commercial granules.

The primary enzyme present in the enzyme granules produced in accordance with the invention is, above all, protease obtained from microorganisms, such as bacteria or fungi. It may be obtained from suitable microorganisms by known fermentation processes which are described, for example, in DE-OSS 19 40 488, 20 44 161, 21 01 803 and 21 21 397, in U.S. Pat. Nos. 3,632,957 and 4,264,738, in European patent application EP 006 638 and in International patent application WO 91/02792. Proteases are commercially available, for example, under the names BLAP®, Savinase®, Esperase®, Maxatase®, Optimase®, Alcalase®, Durazym® or Maxapem®.

The primary enzyme is preferably present in the extrudates according to the invention in quantities of 1% by weight to 6% by weight. If the enzyme granules according to the invention are a protease-containing formulation, their protease activity preferably amounts to between 50,000 protease units (PU, as determined by the method described in Tenside 7 (1970), 125) and 350,000 PU and, more particularly, to between 100,000 PU and 250,000 PU per gram of enzyme granules.

The lipase suitable for use as the secondary enzyme or as a secondary enzyme component in the process according to the invention may be obtained from *Humicola lanuginosa*, as described for example in European patent applications EP 258 068, EP 305 216 and EP 341 947, from Bacillus species, as described for example in International patent application WO 91/16422 or in European patent application EP 384 717, from Pseudomonas species, as described for example in European patent applications EP 468 102, EP 385 401, EP 375 102, EP 334 462, EP 331 376, EP 330 641, EP 214 761, EP 218 272 or EP 204 284 or in International patent application WO 90/10695, from Fusarium species as described, for example, in European patent application EP 130 064, from Rhizopus species as described, for example, in European patent application EP 117 553, or from Aspergillus species as described, for example, in European patent application EP 167 309. Suitable lipases are commercially obtainable, for example, under the names Lipolase®, Lipozym®, Lipomax®, Amano® Lipase, Toyo Jozo® Lipase, Meito® Lipolase and Diosynth® Lipase. Lipase is preferably used in the process according to the invention in such quantities that the multi-enzyme granules contain 1 KLU/g (Kilo Lipase Units per gram according to the Novo standard method based on the enzymatic hydrolysis of tributyrin, as described in Novo Nordisk publication AF 95) to 80 KLU/g, preferably 1.5 KLU/g to 60 KLU/g and more preferably 2 KLU/g to 30 KLU/g.

Multi-enzyme granules containing protease as the primary enzyme and amylase as the secondary enzyme are particularly suitable for use in dishwashing detergents, particularly machine dishwashing detergents. Suitable amylases are commercially available, for example, under the names Maxamyl® and Termamyl®. Amylase is preferably used in the process according to the invention in such quantities that the multi-enzyme granules contain 1 KNU/g (Kilo Novo Units per gram according to the Novo standard method, 1 KNU being the quantity of enzyme which degrades 5.26 g of starch at pH 5.6/37° C., based on the method described by P. Bernfeld in S. P. Colowick and N. D. Kaplan, Methods in Enzymology, Vol. 1, 1955, page 149) to 100 KNU/g, preferably 2 KNU/g to 60 KNU/g and more preferably 5 KNU/g to 50 KNU/g.

The cellulase suitable for use as the secondary enzyme or as a secondary enzyme component may be an enzyme obtainable from bacteria or fungi which has an optimum pH preferably in the mildly acidic to mildly alkaline range of 6 to 9.5. Corresponding cellulases are known, for example, from DE-OSS 31 17 250, 32 07 825, 32 07 847, 33 22 950 or from European patent applications EP 265 832, EP 269 977, EP 270 974, EP 273 125 and EP 339 550. They are preferably used in such quantities that the final multi-enzyme granules have a cellulolytic activity of 50 CEVU/g (Cellulose Viscosity Units per gram based on the enzymatic hydrolysis of carboxymethyl cellulose at pH 9.0/40° C., as described in Novo Nordisk publication AF 253) to 1250 CEVU/g and, preferably, 100 CEVU/g to 1000 CEVU/g.

The production process according to the invention comprises mixing a first enzyme which is present in liquid form, for example in the form of an aqueous fermentation broth optionally freed from insoluble constituents, and which preferably has a water content below 35% by weight and, more particularly, from 5% by weight to 30% by weight with a competitive inhibitor for this enzyme. Such inhibitors include polyhydric alcohols, more particularly glycerol, propylene glycol, amino alcohols, for example mono-, di- and tri-ethanolamine and -propanolamine and mixtures thereof, lower carboxylic acids, for example as known from European patent applications EP 376 705 and EP 378 261, boric acid and alkali metal borates, boric acid/carboxylic acid combinations as known, for example, from European patent application EP 451 921, boric acid esters as known, for example, from International patent application WO 93/11215 or from European patent application EP 511 456, boric acid derivatives as known, for example, from European patent application EP 583 536, calcium salts, for example the calcium/formic acid combination known from European patent EP 28 865, magnesium salts as known, for example, from European patent application EP 378 262 and/or sulfur-containing reducing agents as known, for example, from European patent applications EP 080 748 or EP 080 223. The substances mentioned are preferably used in quantities of 20% by weight to 60% by weight and preferably in quantities of 35% by weight to 50% by weight, based on the resulting mixture of water-containing enzyme and inhibitor.

Suitable carrier materials for the enzyme mixture, which may be incorporated immediately afterwards, but more particularly only after addition of the secondary enzyme, are in principle any organic or inorganic powder-form substances which destroy or only reversibly deactivate the enzymes to a negligible extent, if at all, and which are stable under extrusion conditions. Corresponding substances are, for example, cellulose, maltodextrose, sucrose, invert sugar, glucose, starches, cereal flours, cellulose ethers, alkali metal alumosilicate, more particularly zeolite, layer silicate, for example bentonite or smectite, and water-soluble inorganic or organic salts, for example alkali metal chloride, alkali metal sulfate, alkali metal carbonate or alkali metal acetate, sodium or potassium being the preferred alkali metals. A mixture of starch, cereal flour, powder-form cellulose and sucrose and, optionally, cellulose ether and alkali metal carbonate is preferably used as the carrier material. If the secondary enzyme is used in solid form, it is generally present in the form of a powder or granules made up with such carrier materials. In one embodiment of the process according to the invention, there is no need in this case for the separate addition of carrier material.

The starch suitable as the carrier material or as a component of the carrier material is preferably corn starch, rice starch, potato starch or mixtures thereof, corn starch being particularly preferred. Starch is preferably present in the carrier material for the enzyme mixture in quantities of 20 to 80% by weight and, more preferably, in quantities of 25% by weight to 75% by weight, based on the carrier material as a whole. The sum total of the quantities of starch and flour is preferably not more than 95% by weight and, more particularly, is between 60% by weight and 95% by weight. The cereal flour is in particular a product obtainable from wheat, barley, rye or oats or a mixture of these flours, whole-grain flours being preferred. A whole-grain flour in the context of the invention is understood to be a flour which has not been fully ground and which has been produced from whole non-dehulled grains or which consists at least predominantly of such a product, the rest consisting of fully ground flour or starch. Commercially available wheat flours, such as Type 450 or Type 550, are preferably used. It is also possible to use ground products of the cereals leading to the starches mentioned above providing steps are taken to ensure that the flours have been produced from whole grains. It is known that the flour component of the additive mixture significantly reduces the odor of the enzyme preparation to an extent considerably greater than that achieved by incorporating corresponding starches in the same quantities. Corresponding cereal flour is preferably present in the carrier material for the primary enzyme in quantities of 10% by weight to 35% by weight and, more preferably, in quantities of 15% by weight to 20% by weight.

Granulation aids may be present as additional constituents of the carrier material, including for example cellulose or starch ethers, such as carboxymethyl cellulose, carboxymethyl starch, methyl cellulose, hydroxyethyl cellulose, hydroxypropyl cellulose and corresponding cellulose mixed ethers, gelatine, casein, tragacanth or other water-soluble or readily water-dispersible oligomers or polymers of natural or synthetic origin. The synthetic water-soluble polymers include alkyl or alkenyl polyethoxylates, polyethylene glycols, polyacrylates, polymethacrylates, copolymers of acrylic acid with maleic acid or compounds containing vinyl groups, also polyvinyl alcohol, partly hydrolyzed polyvinyl acetate and polyvinyl pyrrolidone. Polyethylene glycols are preferably selected from those having average molecular weights of 200 to 3,000. If the granulation aids mentioned above are those containing carboxyl groups, they are normally present in the form of their alkali metal salts, more especially their sodium salts. Corresponding granulation aids may be present in the enzyme compounds suitable for the purposes of the invention in quantities of up to 10% by weight and, more particularly, in quantities of 0.5% by weight to 8% by weight, based on the multi-enzyme mixture to be extruded. The degree of substitution in carboxymethyl celluloses preferably used is in the range from 0.8 to 0.95 because particularly strong granules are obtained where corresponding carboxymethyl celluloses are used or smaller quantities are required to obtain granules of a certain strength than where cellulose having a relatively low degree of substitution is used. In addition, by using the above-mentioned carboxymethyl cellulose with a relatively high degree of substitution, a higher throughput through the extruder can be achieved in the extrusion step of the granule production process. The degree of substitution of the carboxymethyl cellulose is understood to be the number of etherified oxygen atoms bearing a carboxymethyl group per saccharide monomer of the cellulose.

The secondary enzyme present in solid or, preferably, liquid form may be added to the primary enzyme afterwards or before addition of the carrier material or granulation aid. The other constituents of the secondary enzyme optionally present in addition to the second enzyme are not critical although—for the preferred use of the enzyme granules according to the invention in detergents and cleaning compositions—typical ingredients of detergents and cleaning compositions or at least substances compatible therewith are preferably present. If the secondary enzyme is added in solid form, i.e. in admixture with carriers or diluents, this added component preferably contains inorganic salt, more particularly alkali metal sulfate and/or chloride, in quantities—based on the secondary enzyme preparation—of 30% by weight to 80% by weight, fibrous or powder-form cellulose in quantities of 2 to 40% by weight and binders, more particularly dextrose, sucrose, polyvinyl alcohol and/or polyvinyl pyrrolidone, in quantities of 0.1% by weight to 15% by weight. Made-up enzyme granules containing the secondary enzyme may also be used in the production process according to the invention. Accordingly, the particle containing the second enzyme may be produced by an extrusion process as described, for example, in International patent application WO 92/11347 or in European patent EP 168 526. Particulate secondary enzymes are preferably produced by pan granulation from an inorganic and/or organic carrier material and aqueous enzyme solution. A corresponding process using inorganic salt and cellulose fibers in the carrier material and water and/or a wax-like substance as binder is described, for example, in German patent DE 27 30 481.

The enzyme granules according to the invention are preferably produced from aqueous primary enzyme fermenter broths which are freed from insoluble impurities, for example by microfiltration. The microfiltration is preferably carried out as crossflow microfiltration using porous tubes with micropores larger than 0.1 μm in size, flow rates of the concentrate solution of more than 2 m/s and a pressure difference to the permeate side of less than 5 bar, as described, for example in European patent application EP 200 032. The microfiltration permeate is then concentrated, preferably by ultrafiltration optionally followed by vacuum evaporation. Concentration is preferably carried out in such a way that water contents of no more than 35% by weight are obtained. The concentrate is mixed with the secondary enzyme and a dry powder-form to granular mixture of the above-described carrier materials or extrusion aids preferably prepared in advance, addition in the reverse order or simultaneous addition also being possible. These additives are preferably selected from the carrier materials and extrusion aids mentioned in such a way that the multi-enzyme extrudate formed has an apparent density of 700 g/l to 1200 g/l. The water content of the mixture to be extruded should be selected so that it can be converted during compounding with stirring and beating tools into granular particles non-tacky at room temperature and can be plastically deformed and extruded under relatively high pressures. The multi-enzyme mixture is then processed in basically known manner in a kneader and an adjoining extruder to form a plastic, substantially homogeneous paste which can undergo an increase in temperature to between 40° C. and 60° C. and, more particularly, to between 45° C. and 55° C. as a result of compounding. The material leaving the extruder is passed through a multiple bore die followed by a cutting blade so that it is reduced to cylindrical particles of predetermined size. The diameter of the bores in the multi-bore die is best from 0.7 mm to 1.2 mm and preferably from 0.8 mm to 1.0 mm. The length-to-thickness ratio of the extrudate is preferably in the range from 0.9 to 1.1:1 and, more preferably, is 1.0:1. The particles present in this form may then be directly incorporated in detergents and cleaning compositions, optionally after a drying step. However, it has been found to be of advantage to spheronize the cylindrical particles leaving the extruder and cutter, i.e. to round them off and to "deflash" them in suitable machines. A corresponding spheronizing process is described, for example, in DE-OSS 21 37 042 and 21 37 043. It is carried out in a machine consisting of a cylindrical container with stationary, fixed side walls and a friction plate rotatably mounted on its base. Machines of this type are marketed under the name of Marumerizer®. After spheronizing, the still moist spherical particles are dried continuously or in batches, preferably in a fluidized bed dryer, at a temperature of preferably 35° C. to 50° C. and, more particularly, at a maximum product temperature of 45° C. to a residual moisture content of 4% by weight to 10% by weight and preferably 5% by weight to 8% by weight if they previously had higher water contents. At this stage of the process, any dust-like fractions smaller than 0.1 mm and, more particularly, 0.4 mm in size occurring during the production of the extrudate and any coarse fractions larger than 2 mm and, more particularly, 1.6 mm in size can be removed by sieving or air separation and optionally returned to the production process. The extrusion process is preferably carried out in such a way that the multi-enzyme extrudates formed have such a particle size distribution that less than 10% by weight and, more particularly, less than 2% by weight of the particles are smaller than 0.2 mm in diameter, 10% by weight to 20% by weight of the particles are 0.2 mm to less than 0.4 mm in diameter and 80% by weight to 90% by weight of the particles are from 0.4 mm to less than 0.8 mm in diameter.

Substances for encapsulating and coating the extrudate particles may be additionally introduced after or preferably during the drying process. To this end, the drying step is preferably carried out by spraying the enzyme-containing particles in a fluidized bed with a typical binder which, in its most simple form, may be water. Other suitable binders are nonionic surfactants and, more particularly, film formers selected from the water-soluble organic polymers mentioned above, for example carboxymethyl cellulose and/or polyethylene glycol, which may be used as such or, more particularly, in the form of aqueous solutions. In addition, dyes or pigments may also be applied to the particles at the agglomeration stage in order to mask or modify any coloration present in the particles which generally emanates from the enzyme concentrate. Titanium dioxide and calcium carbonate have proved to be particularly suitable inert and physiologically safe pigments, being introduced subsequently or preferably together with the binder in the form of an aqueous dispersion. The water introduced with the pigment dispersion or with the binder is removed again during the drying step which is carried out at the same time or which may have to be carried out at a later stage.

It is readily possible by the process according to the invention to obtain multi-enzyme granules which have the enzyme activity for each enzyme present theoretically expected from the activity of the individual enzymes used. In general, more than 90% and, in particular, more than 95% of the expected activity is maintained.

The multi-enzyme granules obtainable in this way are preferably used for the production of solid, above all particulate detergents or cleaning products which may be obtained simply by mixing the multi-enzyme granules with other components typically used in detergents or cleaning products. Surprisingly, however, multi-enzyme granules according to the invention may also be incorporated in liquid or free-flowing and paste-like, water-free or water-containing formulations in which the multi-enzyme granules are insoluble, a distinct increase in the stability of the enzymes in storage by comparison with enzymes introduced in solution being obtained despite the simultaneous presence of incompatible enzymes. The viscosity of liquid formulations such as these is preferably in the range from 100 mPa·s to 60,000 mPa·s and may be adjusted within wide limits through the concentration in which soap and solvents, for example, are used. Protease/amylase granules according to the invention in particular are preferably used in machine dishwashing detergents which are preferably marketed as compacted powders with elevated apparent densities of, preferably, 750 to 1,000 g/l or in tablet form. Corresponding tablets are preferably produced by mixing the multi-enzyme granules with all the other ingredients in a mixer and tabletting the resulting mixture in conventional tablet presses, for example eccentric presses or rotary presses, under pressures of $200 \cdot 10^5$ Pa to $1500 \cdot 10^5$ Pa. Breakage-resistant tablets which still dissolve sufficiently quickly under in-use conditions are readily obtained in this way, typically with flexural strengths in excess of 150 N. A correspondingly produced tablet preferably has a weight of 15 g to 40 g and, more particularly, 20 g to 30 g for a diameter of 35 mm to 40 mm.

For incorporation in particulate detergents and cleaning formulations, the enzyme granules preferably have average particle sizes of 0.9 mm to 1.8 mm and, more preferably, in the range from 1.0 mm to 1.5 mm. The granules produced in accordace with the invention preferably contain less than 5% by weight and, more preferably, at most 1% by weight of particles with sizes outside the 0.2 mm to 1.6 mm range.

The enzyme preparation obtained in accordance with the invention consists of substantially rounded dust-free particles which generally have an apparent density of around 650 to 1050 grams per liter and, more particularly, 700 to 880 grams per liter. The granules produced in accordance with the invention are distinguished by very high stability in storage, particularly at temperatures above room temperature and at high atmospheric humidity levels, which—although enzymes capable of reacting with one another are present—generally exceeds even the stability in storage of individual enzymes made up separately from one another. This applies both to the enzyme granules according to the invention and to the enzyme granules according to the invention incorporated in particulate detergents or cleaning formulations. Another advantage of the enzyme granules according to the invention is their dissolving behavior under in-use conditions in the wash liquor in which all the enzymes present can be simultaneously released and can develop their cleaning effect. In a preferred embodiment, the granules according to the invention release at least 90% of their enzyme activity in water at 25° C. within 3 minutes and, more particularly, within 70 seconds to 2.5 minutes.

Detergents or cleaning formulations containing multi-enzyme granules according to the invention or produced by the process according to the invention may contain other typical ingredients of such formulations which do not undesirably interact with the enzymes. The multi-enzyme granules are preferably incorporated in detergents or cleaning formulations in quantities of 0.1% by weight to 5% by weight and, more particularly, in quantities of 0.5% by weight to 2.5% by weight.

It has surprisingly been found that enzyme granules having the properties described above synergistically influence the effect of certain other ingredients of detergents and cleaning compositions and that, conversely, the effect of the enzymes present in the multi-enzyme granules is synergistically enhanced by certain other detergent ingredients. These effects occur in particular in the case of nonionic surfactants, in the case of soil-releasing copolyesters, particularly those containing terephthalic acid units, in the case of water-insoluble inorganic builders, in the case of water-soluble inorganic and organic builders, more particularly based on oxidized carbohydrates, in the case of peroxygen-based bleaching agents, more particularly alkali metal percarbonate, and in the case of synthetic anionic surfactants of the sulfate and sulfonate type, but only to a negligible extent, if at all, in the case of alkyl benzene sulfonates, so that the ingredients mentioned are preferably used together with multi-enzyme granules according to the invention.

In one preferred embodiment, a corresponding formulation contains nonionic surfactant selected from fatty alkyl polyglycosides, fatty alkyl polyalkoxylates, more particularly ethoxylates and/or propoxylates, fatty acid polyhydroxyamides and/or ethoxylation and/or propoxylation products of fatty alkyl amines, vicinal diols, fatty acid alkyl esters and/or fatty acid amides or mixtures thereof, more particularly in quantities of 2% by weight to 25% by weight.

Another embodiment of such formulations is characterized by the presence of synthetic anionic surfactant of the sulfate and/or sulfonate type, more particularly fatty alkyl sulfate, fatty alkyl ether sulfate, sulfofatty acid esters and/or sulfofatty acid disalts, more particularly in a quantity of 2% by weight to 25% by weight. The anionic surfactant is preferably selected from the alkyl or alkenyl sulfates and/or the alkyl or alkenyl ether sulfates in which the alkyl or alkenyl group contains 8 to 22 carbon atoms and, more particularly, 12 to 18 carbon atoms.

Suitable nonionic surfactants are the alkoxylates, more particularly the ethoxylates and/or propoxylates, of saturated or mono- to polyunsaturated linear or branched alcohols containing 10 to 22 and preferably 12 to 18 carbon atoms. The degree of alkoxylation of the alcohols is generally between 1 and 20 and preferably between 3 and 10. They may be prepared in known manner by reaction of the corresponding alcohols with the corresponding alkylene oxides. Derivatives of the fatty alcohols are particularly suitable, although their branched-chain isomers, particularly so-called oxoalcohols, may also be used for the production of suitable alkoxylates. Accordingly, the alkoxylates, more particularly the ethoxylates, of primary alcohols containing linear groups, more particularly dodecyl, tetradecyl, hexadecyl or octadecyl groups and mixtures thereof are suitable. Corresponding alkoxylation products of alkyl amines, vicinal diols and carboxylic acid amides, which correspond to the alcohols mentioned in regard to the alkyl moiety, may also be used. Other suitable nonionic surfactants are the ethylene oxide and/or propylene oxide insertion products of fatty acid alkyl esters, which may be produced by the process described in International patent application WO 90/13533, and the fatty acid polyhydroxyamides which may be produced by the processes according to U.S. Pat. Nos. 1,985,424, 2,016,962 and U.S. Pat. No. 2,703,798 and International patent application WO 92/06984. So-called alkyl polyglycosides suitable for incorporation in the formulations according to the invention are compounds corresponding to the general formula $(G)_n$—$OR^1$ where $R^1$ is an alkyl or alkenyl group containing 8 to 22 carbon atoms, G is a glycose unit and n is a number of 1 to 10. Corresponding compounds and their production are described, for example, in European patent applications EP 92 355, EP 301 298, EP 357 969 and EP 362 671 or U.S. Pat. No. 3,547,828. The glycoside component $(G)_n$ is an oligomer or polymer of naturally occurring aldose or ketose monomers, including in particular glucose, mannose, fructose, galactose, talose, gulose, altrose, allose, idose, ribose, arabinose, xylose and lyxose. The oligomers consisting of such glycoside-bonded monomers are characterized not only by the type but also by the number of sugars present in them, the so-called degree of oligomerization. The degree of oligomerization n as an analytically determined quantity is generally a broken number, assuming a value of 1 to 10 and, in the case of the glycosides preferably used, a value below 1.5 and, more particularly, between 1.2 and 1.4. Glucose is the preferred monomer by virtue of its ready availability. The alkyl or alkenyl group $R^1$ of the glycosides also preferably emanates from readily available derivatives of renewable raw materials, more particularly from fatty alcohols, although branched-chain isomers thereof, more particularly so-called oxoalcohols, may also be used for the production of suitable glycosides. Accordingly, primary alcohols containing linear octyl, decyl, dodecyl, tetradecyl, hexadecyl or octadecyl groups and mixtures thereof are particularly suitable. Particularly preferred alkyl glycosides contain a cocofatty alkyl group, i.e. mixtures with—essentially—$R^1$=dodecyl and $R^1$=tetradecyl.

Nonionic surfactant is preferably present in formulations containing multi-enzyme granules according to the invention in quantities of 1 to 30% by weight and, more preferably, in quantities of 1% by weight to 25% by weight.

The formulations in question may contain other surfactants instead of or in addition to those mentioned above, preferably synthetic anionic surfactants of the sulfate or sulfonate type, in quantities of preferably not more than 20% by weight and, more preferably, in quantities of 0.1% by weight to 18% by weight, based on the formulation as a whole. Alkyl and/or alkenyl sulfates containing 8 to 22 carbon atoms, in which an alkali metal, ammonium or alkyl- or hydroxyalkyl-substituted ammonium ion is present as countercation, are mentioned as particularly suitable synthetic anionic surfactants for use in such formulations. The derivatives of fatty alcohols containing in particular 12 to 18 carbon atoms and branched-chain analogs thereof, so-called oxoalcohols, are preferred. The alkyl and alkenyl sulfates may be produced in known manner by reaction of the corresponding alcohol component with a typical sulfating agent, more particularly sulfur trioxide or chlorosulfonic acid, and subsequent neutralization with alkali metal, ammonium or alkyl- or hydroxyalkyl-substituted ammonium bases. Corresponding alkyl and/or alkenyl sulfates are preferably present in the formulations containing multi-enzyme granules according to the invention in quantities of 0.1% by weight to 20% by weight and, more preferably, in quantities of 0.5% by weight to 18% by weight.

Other suitable surfactants of the sulfate type are the sulfated alkoxylation products of the alcohols mentioned, so-called ether sulfates. These ether sulfates preferably contain 2 to 30 and, more preferably, 4 to 10 ethylene glycol groups per molecule. Suitable anionic surfactants of the sulfonate type include the α-sulfoesters obtainable by reaction of fatty acid esters with sulfur trioxide and subsequent neutralization, more particularly the sulfonation products derived from fatty acids containing 8 to 22 carbon atoms, preferably 12 to 18 carbon atoms, and linear alcohols containing 1 to 6 carbon atoms and preferably 1 to 4 carbon atoms and the sulfofatty acids obtainable therefrom by formal saponification.

Other optional surface-active ingredients are soaps, saturated fatty acid soaps, such as the salts of lauric acid, myristic acid, palmitic acid or stearic acid, and soaps derived from natural fatty acid mixtures, for example coconut oil, palm kernel oil or tallow fatty acids, being suitable. Soap mixtures of which 50% by weight to 100% by weight consist of saturated $C_{12-18}$ fatty acid soaps and up to 50% by weight of oleic acid soap are particularly preferred. Soap is preferably present in quantities of 0.1% by weight to 5% by weight. However, larger quantities of soap, generally up to 20% by weight, may also be present, particularly in liquid formulations containing multi-enzyme granules according to the invention.

In another embodiment, a formulation containing multi-enzyme granules according to the invention contains water-soluble and/or insoluble builders selected in particular from alkali metal alumosilicate, crystalline alkali metal silicate with a modulus of more than 1, monomeric polycarboxylate, polymeric polycarboxylate and mixtures thereof, more particularly in quantities of 2.5% by weight to 60% by weight.

A formulation containing multi-enzyme granules according to the invention preferably contains 20% by weight to 55% by weight of water-soluble and/or water-insoluble organic and/or inorganic builders. The water-soluble organic builders include in particular those from the class of polycarboxylic acids, more particularly citric acid and sugar acids, and polymeric (poly)carboxylic acids, more particularly the polycarboxylates obtainable by oxidation of polysaccharides according to International patent application WO 93/16110, polymeric acrylic acids, methacrylic acids, maleic acids and copolymers thereof which may also contain small quantities of polymerizable substances with no carboxylic acid functionality in copolymerized form. The relative molecular weight of the homopolymers of unsaturated carboxylic acids is generally between 5,000 and 200,000 while the relative molecular weight of the copolymers is between 2,000 and 200,000 and preferably between 50,000 and 120,000, based on free acid. A particularly preferred acrylic acid/maleic acid copolymer has a relative molecular weight of 50,000 to 100,000. Suitable, albeit less preferred, compounds of this class are copolymers of acrylic acid or methacrylic acid with vinyl ethers, such as vinyl methyl ethers, vinyl esters, ethylene, propylene and styrene, in which the percentage content of the acid is at least 50% by weight. Other suitable water-soluble organic builders are terpolymers containing two carboxylic acids and/or salts thereof as monomers and vinyl alcohol and/or a vinyl alcohol derivative or a carbohydrate as the third monomer. The first acidic monomer or its salt is derived from a monoethylenically unsaturated $C_{3-8}$ carboxylic acid and preferably from a $C_{3-4}$ monocarboxylic acid, more particularly from (meth)acrylic acid. The second acidic monomer or its salt may be a derivative of a $C_{4-8}$ dicarboxylic acid, preferably a $C_{4-8}$ dicarboxylic acid, maleic acid being particularly preferred. In this case, the third monomeric unit is derived from vinyl alcohol and/or preferably an esterified vinyl alcohol. Vinyl alcohol derivatives in the form of an ester of short-chain carboxylic acids, for example $C_{1-4}$ carboxylic acids, with vinyl alcohol are particularly preferred. Preferred terpolymers contain 60% by weight to 95% by weight and, more particularly, 70% by weight to 90% by weight of (meth)acrylic acid or (meth)acrylate, preferably acrylic acid or acrylate, and maleic acid or maleate and 5% by weight to 40% by weight and preferably 10% by weight to 30% by weight of vinyl alcohol and/or vinyl acetate. Terpolymers in which the ratio by weight of (meth)acrylic acid or (meth)acrylate to maleic acid or maleate is between 1:1 and 4:1, preferably between 2:1 and 3:1 and more preferably between 2:1 and 2.5:1 are most particularly preferred. Both the quantities and the ratios by weight mentioned are based on the acids. The second acidic monomer or its salt may also be a derivative of an allyl sulfonic acid substituted in the 2-position by an alkyl group, preferably a $C_{1-4}$ alkyl group, or by an aromatic radical preferably derived from benzene or benzene derivatives. Preferred terpolymers contain 40% by weight to 60% by weight and, more particularly, 45 to 55% by weight of (meth)acrylic acid or (meth)acrylate, preferably acrylic acid or acrylate, 10% by weight to 30% by weight and preferably 15% by weight to 25% by weight of methallyl sulfonic acid or methallyl sulfonate and, as the third monomer, 15% by weight to 40% by weight and preferably 20% by weight to 40% by weight of a carbohydrate. This carbohydrate may be, for example, a mono-, di-, oligo- or polysaccharide, mono-, di- or oligosaccharides being preferred and sucrose being particularly preferred. Predetermined weak spots are presumably incorporated in the polymer through the use of the third monomer, being responsible for the ready biodegradability of the polymer. These polymers may be prepared in particular by the processes described in German patent DE 42 21 381 and in German patent application P 43 00 772.4 and generally have a relative molecular weight in the range from 1,000 to 200,000, preferably in the range from 200 to 50,000 and more preferably in the range from 3,000 to 10,000. They may be used in the form of aqueous solutions, preferably in the form of 30 to 50% by weight aqueous solutions, especially for the production of liquid formulations. All the polycarboxylic acids mentioned are generally used in the form of their water-soluble salts, more particularly their alkali metal salts.

The organic builders in question are preferably present in quantities of up to 40% by weight, more preferably in quantities of up to 25% by weight and most preferably in quantities of 1% by weight to 5% by weight. Quantities near the upper limit mentioned are preferably used in paste-form or liquid formulations, more particularly water-containing formulations, in which the multi-enzyme granules according to the invention are present.

Suitable water-insoluble, water-dispersible inorganic builders are, in particular, crystalline or amorphous alkali metal alumosilicates which are used in quantities of up to 50% by weight, preferably in quantities of not more than 40% by weight and, in liquid formulations in particular, in quantities of 1% by weight to 5% by weight. Among these builders, detergent-quality crystalline alumosilicates, more especially zeolite NaA and optionally NaX, are particularly preferred. Quantities near the upper limit mentioned are preferably used in solid particulate formulations. Suitable alumosilicates in particular contain no particles larger than 30 µm in size, at least 80% by weight preferably consisting of particles less than 10 µm in size. Their calcium binding capacity, which may be determined in accordance with German patent DE 24 12 837, is in the range from 100 to 200 mg CaO per gram. Suitable substitutes or partial substitutes for the alumosilicate mentioned are crystalline alkali metal silicates which may be present on their own or in the form of mixtures with amorphous silicates. The alkali metal silicates suitable as builders in the formulations preferably have a molar ratio of alkali metal oxide to $SiO_2$ of less than 0.95 and, more particularly, in the range from 1:1.1 to 1:12 and may be present in amorphous or crystalline form. Preferred alkali metal silicates are the sodium silicates, more particularly the amorphous sodium silicates, with a molar $Na_2O$ to $SiO_2$ ratio of 1:2 to 1:2.8. Amorphous alkali metal silicates such as these are commercially available, for example, under the name of Portil®. Those with a molar $Na_2O:SiO_2$ ratio of 1:1.9 to 1:2.8 may be produced by the process according to European patent application EP 0 425 427. They are preferably added as a solid and not in the form of a solution in the production process. Preferred crystalline silicates which may be present individually or in the form of a mixture with amorphous silicates are crystalline layer silicates with the general formula $Na_2Si_xO_{2x+1} \cdot yH_2O$, in which x—the so-called modulus—is a number of 1.9 to 4 and y is a number of 0 to 20, preferred values for x being 2, 3 or 4. Crystalline layer silicates corresponding to this general formula are described, for example, in European patent application EP 0 164 514. Preferred crystalline layer silicates are those in which x in the general formula mentioned assumes a value of 2 or 3. β- and δ-sodium disilicates ($Na_2Si_2O_5 \cdot yH_2O$) are particularly preferred, β-sodium disilicate being obtainable for example by the process described in International patent application WO 91/08171. δ-Sodium silicates with a modulus of 1.9 to 3.2 may be prepared in accordance with Japanese patent applications JP 04/238 809 or JP 04/260 610. Substantially water-free crystalline alkali metal silicates corresponding to the above general formula, where x is a number of 1.9 to 2.1, which have been prepared from amorphous alkali metal silicates as described in European patent applications EP 0 548 599, EP 0 502 325 and EP 0 452 428, may also be used in formulations containing multi-enzyme granules according to the invention. Another preferred embodiment of formulations according to the invention is characterized by the use of a crystalline sodium layer silicate with a modulus of 2 to 3 which may be produced from sand and soda by the process according to European patent application EP 0 436 835. Crystalline sodium silicates with a modulus of 1.9 to 3.5 obtainable by the process according to European patents EP 0 164 552 and/or EP 0 293 753 are used in another preferred embodiment of detergents or cleaning formulations containing multi-enzyme granules according to the invention. Their content of alkali metal silicates is preferably between 1% by weight and 50% by weight and more preferably between 5% by weight and 35% by weight, based on water-free active substance. If alkali metal alumosilicate, more particularly zeolite, is present as an additional builder, the alkali metal silicate content is preferably 1% by weight to 15% by weight and more preferably 2% by weight to 8% by weight, based on water-free active substance. In this case, the ratio by weight of alumosilicate to silicate, based on water-free active substances, is preferably 4:1 to 10:1. In formulations containing both amorphous and crystalline alkali metal silicates, the ratio by weight of amorphous alkali metal silicate to crystalline alkali metal silicate is preferably 1:2 to 2:1 and more preferably 1:1 to 2:1.

In addition to the inorganic builder mentioned, other water-soluble or water-insoluble inorganic substances may be used in the formulations containing multi-enzyme granules according to the invention. Alkali metal carbonates, alkali metal hydrogen carbonates and alkali metal sulfates and mixtures thereof are suitable in this regard. This additional inorganic material may be present in quantities of up to 70% by weight, but is preferably absent altogether.

The formulations may additionally contain other ingredients typical of detergents and cleaning formulations. These optional ingredients include in particular bleaching agents, bleach activators, heavy metal complexing agents, for example aminopolycarboxylic acids, aminohydroxypolycarboxylic acids, polyphosphonic acids and/or aminopolyphosphonic acids, redeposition inhibitors, for example cellulose ethers, dye transfer inhibitors, for example polyvinyl pyrrolidone or polyvinyl pyridine-N-oxide, foam inhibitors, for example organopolysiloxanes or paraffins, solvents and optical brighteners, for example stilbene disulfonic acid derivatives. Formulations containing multi-enzyme granules according to the invention contain up to 1% by weight and, more particularly, from 0.01% by weight to 0.5% by weight of optical brighteners, more particularly compounds from the class of substituted 4,4'-bis-(2,4,6-triamino-s-triazinyl)-stilbene-2,2'-disulfonic acids, up to 5% by weight and, more particularly, from 0.1% by weight to 2% by weight of heavy metal complexing agents, more particularly aminoalkylene phosphonic acids and salts thereof, up to 3% by weight and, more particularly, 0.5% by weight to 2% by weight of redeposition inhibitors and up to 2% by weight and, more particularly, from 0.1% by weight to 1% by weight of foam inhibitors, the parts by weight mentioned being based on the formulation as a whole.

Apart from water, solvents which are used in particular in liquid formulations containing multi-enzyme granules according to the invention and which may also be present in the liquid primary and/or secondary enzyme in the production process for the multi-enzyme granules according to the invention are preferably water-miscible solvents, including lower alcohols, for example ethanol, propanol, isopropanol and the isomeric butanols, glycerol, lower glycols, for example ethylene and propylene glycol, and the ethers derived from the classes of compounds mentioned. The multi-enzyme granules are present in undissolved form, i.e. in solid granular form, in these liquid formulations.

The typical enzyme stabilizers optionally present, particularly in liquid formulations according to the invention, include amino alcohols, for example mono-, di-, triethanolamine and -propanolamine and mixtures thereof, lower carboxylic acids as known, for example, from European patent applications EP 376 705 and EP 378 261, boric acid or alkali metal borates, boric acid/carboxylic acid combinations as known, for example, from European patent application EP 451 921, boric acid esters as known, for example, from International patent application WO 93/11215 or European patent application EP 511 456, boric acid derivatives as known, for example, from European patent application EP 583 536, calcium salts, for example the calcium/formic acid combination known from European patent EP 28 865, magnesium salts as known, for example, from European patent application EP 378 262 and/or sulfur-containing reducing agents as known, for example, from European patent applications EP 080 748 or EP 080 223.

Suitable foam inhibitors include long-chain soaps, more particularly behenic soap, fatty acid amides, paraffins, waxes, microcrystalline waxes, organopolysiloxanes and mixtures thereof which may additionally contain microfine, optionally silanized or otherwise hydrophobicized silica. For use in particulate formulations, these foam inhibitors are preferably fixed to granular water-soluble carriers as described, for example, in DE-OS 34 36 194, in European patent applications EP 262 588, EP 301 414, EP 309 931 or European patent EP 150 386.

In addition, a formulation containing multi-enzyme granules according to the invention may contain redeposition inhibitors. The function of redeposition inhibitors is to keep the soil detached from the fibers suspended in the liquid and thus to prevent discoloration of the fibers. Redeposition inhibitors include water-soluble generally organic colloids, for example the water-soluble salts of polymeric carboxylic acids, glue, gelatin, salts of ether carboxylic acids or ether sulfonic acids of starch or cellulose or salts of sulfuric acid esters of cellulose or starch. Water-soluble polyamides containing acidic groups are also suitable for this purpose. Soluble starch preparations and other starch products than those mentioned above, for example partly hydrolyzed starch, may also be used. Sodium carboxymethyl cellulose, methyl cellulose, methyl hydroxyethyl cellulose and mixtures thereof are preferably used.

Another embodiment of a formulation containing multi-enzyme granules according to the invention contains bleaching agents based on peroxygen, more particularly in quantities of 5% by weight to 70% by weight, and optionally bleach activators, more particularly in quantities of 2% by weight to 10% by weight. The bleaching agents in question are the per compounds generally used in detergents, such as hydrogen peroxide, perborate which may be present as tetrahydrate or monohydrate, percarbonate, perpyrophosphate and persilicate which are generally present as alkali metal salts, more particularly sodium salts. These bleaching agents are preferably present in detergents containing multi-enzyme granules according to the invention in quantities of up to 25% by weight, more preferably in quantities of up to 15% by weight and most preferably in quantities of 5% by weight to 15% by weight, based on the detergent as a whole. The optional bleach activators include the N- or O-acyl compounds normally used, for example polyacylated alkylenediamines, more particularly tetraacetyl ethylenediamine, acylated glycol urils, more particularly tetraacetyl glycol uril, N-acylated hydantoins, hydrazides, triazoles, urazoles, diketopiperazines, sulfuryl amides and cyanurates, also carboxylic anhydrides, more particularly phthalic anhydride, carboxylic acid esters, more particularly sodium isononanoyl phenol sulfonate, and acylated sugar derivatives, more particularly pentaacetyl glucose. To avoid interaction with the per compounds in storage, the bleach activators may have been coated or granulated in known manner with shell-forming substances, tetraacetyl ethylenediamine with mean particle sizes of 0.01 mm to 0.8 mm granulated with carboxymethyl cellulose and obtainable, for example, by the process described in European patent EP 037 026 and/or granulated 1,5-diacetyl-2,4-dioxohexahydro-1,3,5-triazine obtainable by the process described in German patent DD 255 884 being particularly preferred. These bleach activators are preferably present in detergents in quantities of up to 8% by weight and, more particularly, in quantities of 2% by weight to 6% by weight, based on the detergent as a whole.

Finally, another embodiment of a formulation containing multi-enzyme granules according to the invention is characterized by the presence of soil release agents based on copolyesters of dicarboxylic acids and glycols which may be present in particular in quantities of 0.01 to 5% by weight. Soil release agents which are particularly effective by virtue of their chemical similarity to polyester fibers, but which are also capable of developing the required effect in fabrics of other materials are copolyesters containing dicarboxylic acid units, alkylene glycol units and polyalkylene glycol units. Soil-releasing copolyesters of the type mentioned and their use in detergents have been known for some time. For example, DE-OS 16 17 141 describes a washing process using polyethylene terephthalate/polyoxyethylene glycol copolymers. DE-OS 22 00 911 relates to detergents containing nonionic surfactant and a copolymer of polyoxyethylene glycol and polyethylene terephthalate. DE-OS 22 53 063 describes acidic textile finishing formulations which contain a copolymer of a dibasic carboxylic acid and an alkylene or cycloalkylene polyglycol and optionally an alkylene or cycloalkylene glycol. European patent EP 066 944 relates to textile treatment formulations containing a copolyester of ethylene glycol, polyethylene glycol, aromatic dicarboxylic acid and sulfonated aromatic dicarboxylic acid in certain molar ratios. European patent EP 185 427 describes methyl- or ethyl-end-capped polyesters containing ethylene and/or propylene terephthalate and polyethylene oxide terephthalate units and detergents containing this soil-releasing polymer. European patent EP 241 984 relates to a polyester containing substituted ethylene units and glycerol units in addition to oxyethylene groups and terephthalic acid units. These soil-releasing polyesters are preferably present in formulations containing multi-enzyme granules according to the invention in quantities of 0.1% by weight to 2.5% by weight and more preferably in quantities of 0.2% by weight to 2% by weight.

A corresponding detergent or cleaning formulation may also contain enzymes which have to be separately added, i.e. which are not incorporated through the multi-enzyme granules according to the invention. However, all enzymes present are preferably incorporated in the multi-enzyme granules.

In one preferred embodiment, a formulation in which the multi-enzyme granules according to the invention or produced in accordance with the invention are incorporated is particulate and contains 20% by weight to 55% by weight of inorganic builder, up to 15% by weight and, more particularly, 2% by weight to 12% by weight of water-soluble organic builder, 2.5% by weight to 20% by weight of synthetic anionic surfactant, 1% by weight to 20% by weight of nonionic surfactant, up to 25% by weight and, more particularly, from 1% by weight to 15% by weight of bleaching agent, up to 8% by weight and, more particularly, from 0.5% by weight to 6% by weight of bleach activator and up to 20% by weight and, more particularly, from 0.1% by weight to 15% by weight of inorganic salts, more particularly alkali metal carbonate and/or sulfate.

In another preferred embodiment, a powder-form detergent intended in particular for use as a light-duty detergent contains 20% by weight to 55% by weight of inorganic builder, up to 15% by weight and, more particularly, from 2% by weight to 12% by weight of water-soluble organic builder, from 4% by weight to 24% by weight of nonionic surfactant, up to 15% by weight and, more particularly, from 1% by weight to 10% by weight of synthetic anionic surfactant, up to 65% by weight and, more particularly, from 1% by weight to 30% by weight of inorganic salts, more particularly alkali metal carbonate and/or sulfate and neither bleaching agent nor bleach activator.

Another preferred embodiment is a liquid formulation containing 5% by weight to 35% by weight of water-soluble organic builder, up to 15% by weight and, more particularly, from 0.1% by weight to 5% by weight of water-insoluble inorganic builder, up to 15% by weight and, more particularly, from 0.5% by weight to 10% by weight of synthetic anionic surfactant, from 1% by weight to 25% by weight of nonionic surfactant, up to 15% by weight and, more particularly, from 4% by weight to 12% by weight of soap and up to 30% by weight and, more particularly, from 1% by weight to 25% by weight of water and/or water-miscible solvent.

EXAMPLES

Example 1

A biomass-containing fermenter broth containing around 65,000 protease units per gram (PU/g) was obtained by fermentation of *Bacillus licheniformis* (ATCC 53926)—modified by the process described in International patent application WO 91/02792 by transformation of a gene sequence from *Bacillus lentus* DSM 5483—using the process described in German patent DE 29 25 427. The fermenter broth was concentrated to a protease content of 700,000 PU/g by decantation, crossflow microfiltration, ultrafiltration (cutoff limit at molecular weight 10,000) and subsequent concentration by evaporation in vacuo by the process described in International patent application WO 92/11347. 50 Parts by weight of propylene glycol were then added as inhibitor. The primary enzyme solution was then mixed with the commercially available liquid enzyme formulations listed in Table 1. 45 Parts by weight of cellulose powder (Technocel® 30, a product of Cellulose Füllstoff Fabrik), 35 parts by weight of sucrose, 120 parts by weight of Na carboxymethyl cellulose (Tylose®, a product of Hoechst AG), 50 parts by weight of polyethylene glycol (average molecular weight 2,000), 300 parts by weight of corn starch and 130 parts by weight of wheat flour were then added to the enzyme mixture in a mixer equipped with a rotating beating tool and the resulting mixture was homogenized in an externally cooled kneader. The plastic material was extruded in an extruder equipped with a multi-bore extrusion die (bore diameter 0.8 mm) and a rotating blade. The 0.8 mm long enzyme extrudates characterized by their enzyme composition in Table 1 were obtained and were then powdered with 3 parts by weight of calcium carbonate and spheronized and deflashed for about 1 minute in a spheronizing machine (Marumerizer®) to form uniformly rounded particles. The material leaving the spheronizer was dried in a fluidized-bed dryer at temperatures of 40° C. to 45° C. and coated with 150 parts by weight of a coating material consisting of $TiO_2$, stearyl alcohol and 40x ethoxylated castor oil. Particles smaller than 0.4 mm and larger than 1.6 mm in size (less than 1% by weight of all the particles) were subsequently removed by sieving.

TABLE 1

Enzyme Content of the Extrudates (Parts by Weight)

|  | E1 | E2 | E3 | E4 |
| --- | --- | --- | --- | --- |
| Protease broth | 190 | 190 | 300 | 190 |
| Amylase[a] | 140 | — | 20 | — |
| Lipase[b] | — | 140 | — | — |
| Cellulase[c] | — | — | — | 140 |

[a] Termamyl® 300 L (liquid formulation; a product of Novo Nordisk)
[b] Lipolase® 100 L (liquid formulation; a product of Novo Nordisk)
[c] Celluzyme® 700 L (liquid formulation; a product of Novo Nordisk)

Example 2

The multi-enzyme granules E2 produced in Example 1 were mixed in a quantity of 1 part by weight with 99 parts by weight of a detergent with an apparent density of 780 g/l produced in accordance with WO 91/02047 containing 18% by weight of sodium alkyl benzene sulfonate, 3% by weight of nonionic surfactant (Dehydol®), 16% by weight of sodium perborate, 29% by weight of zeolite NaA, 5% by weight of sodium carbonate, 5% by weight of polymeric polycarboxylate (Sokalan CP 5, a product of BASF), 6% by weight of tetraacetyl ethylenediamine, 3% by weight of plasticizing aid (40x ethoxylated fatty alcohol) and—as the balance to 100% by weight—water (formulation W1). A mixture C1 which contained the same percentage of detergent and enzymes, but in which the two enzymes were distributed between two separate particles (protease granules according to International patent application WO 92/11347; Lipolase® 100 T, a product of Novodisk) was produced for comparison. The two formulations were stored for 6 weeks at 40° C./80% relative air humidity. The enzyme activities (in arbitrary units) before and after storage are shown in Table 2 below. It can be seen that, in the detergent containing the multi-enzyme granules according to the invention, the stability of the enzymes present in one particle is significantly higher than when the enzymes are present in separate particles. The same surprising finding also applies to the multi-enzyme extrudates E1, E3 and E4 of Example 1.

TABLE 2

Enzyme Activities

|  |  | Protease Activity | Lipase Activity |
| --- | --- | --- | --- |
| W1: | Start | 142 | 38 |
|  | after 6 weeks' storage | 136 | 34 |
| C1: | Start | 117 | 75 |
|  | after 6 weeks' storage | 75 | 52 |

We claim:

1. A process for the production of enzyme granules consisting essentially of at least two different enzymes, a competitive inhibitor, and a carrier material, comprising the steps of:

A) mixing an aqueous liquid containing a first enzyme with at least one competitive inhibitor for this enzyme to form a reversibly inactivated primary enzyme composition;

B) mixing the primary enzyme composition with at least one second enzyme different from the first enzyme to form an enzyme mixture;

C) mixing the enzyme mixture with an inorganic carrier material, an organic carrier material, or both;

D) extruding the resulting mixture from step C) through a multi-bore die followed by a cutting unit; and E) if the resulting cut extrudate has a water content of more than about 10% by weight, drying the resulting cut extrudate to a residual water content of not more than about 10% by weight.

2. The process of claim 1 wherein in step B) at least one of the at least one second enzyme is incompatible with the first enzyme.

3. The process of claim 1 wherein in step A) the aqueous liquid containing a first enzyme is a fermentation broth which has been freed from insoluble constituents and concentrated.

4. The process of claim 1 wherein following step D) and before step E), the extrudate is spheronized.

5. The process of claim 4 wherein the extrudate in step D) has a particle-size distribution such that less than about 10% by weight thereof are smaller than 0.2 mm in diameter, from about 10 to about 20% by weight are from about 0.2 to less than 0.4 mm in diameter, and from about 80 to about 90% by weight are from about 0.4 to less than about 0.8 mm in diameter.

6. The process of claim 1 wherein following or during step E), the extrudate particles are contacted with materials for encapsulating and coating the particles.

7. The process of claim 1 wherein in step B) the at least one second enzyme is in the form of a mixture with a carrier material.

8. The process of claim 7 wherein the carrier material in step B) comprises from about 30 to about 80% by weight of an inorganic salt, from about 2 to about 40% by weight of a fibrous or powder-form cellulose, and from about 0.1 to about 15% by weight of a binder.

9. The process of claim 1 wherein in step A) the competitive inhibitor is at least one inhibitor selected from the group consisting of a polyhydric alcohol, a lower carboxylic acid, boric acid, an alkali metal borate, a boric acid ester, a boric acid derivative, a calcium salt, a magnesium salt, and a sulfur-containing reducing agent.

10. The process of claim 1 wherein the first enzyme is protease and the at least one second enzyme is selected from the group consisting of amylase, lipase, cellulase, hemicellulase, oxidase, peroxidase, and mixtures of the foregoing.

11. The process of claim 10 wherein the protease is present in such quantity that the multi-enzyme granules obtained have a protease activity of from about 50,000 PU/g to about 350,000 PU/g.

12. The process of claim 10 wherein the enzyme granules have an amylase activity of from about 1 KNU/g to about 100 KNU/g.

13. The process of claim 10 wherein the enzyme granules have a lipase activity of from about 1 KLU/g to about 80 KLU/g.

14. The process of claim 10 wherein the enzyme granules have a cellulase activity of from about 50 CEVU/g to about 1250 CEVU/g.

15. The process of claim 1 wherein in step C) the carrier material is at least one carrier material selected from the group consisting of cellulose, maltodextrose, sucrose, invert sugar, glucose, a starch, a cereal flour, a cellulose ether, an alkali metal alumosilicate, a layer silicate, and a water-soluble inorganic or organic salt.

16. The process of claim 1 wherein in step E) the extrudate has a water content of from about 5 to about 8% by weight.

17. The process of claim 1 wherein the carrier material in step C) comprises from about 20 to about 80% by weight of a starch, and from about 10 to about 35% by weight of a cereal flour, based on the weight of the carrier material.

18. The process of claim 17 wherein the total weight of starch and cereal flour is from about 60 to about 95% by weight of the carrier material.

19. The process of claim 1 wherein the extrudate in step D) has a length-to-thickness ratio of from about 0.9:1 to about 1.1:1.

20. The enzyme granules produced by the process of claim 1.

21. In a detergent or cleaning composition, the improvement wherein the composition contains from about 0.1 to about 5% by weight of the enzyme granules produced by the process of claim 1.

22. The detergent or cleaning composition of claim 21 wherein the composition contains from about 0.5 to about 2.5% by weight of the enzyme granules.

23. A process for the production of enzyme granules containing at least two different enzymes comprising the steps of:

A) mixing an aqueous liquid containing a first enzyme with a reversible competitive inhibitor for this enzyme to form a primary enzyme composition;

B) mixing the primary enzyme composition with at least one second enzyme different from the first enzyme; and wherein the at least one second enzyme is in the form of a mixture with an inorganic carrier material, an organic carrier material, or both;

C) extruding the resulting mixture from step B) through a multi-bore die followed by a cutting unit; and D) if the resulting cut extrudate has a water content of more than about 10% by weight, drying the resulting cut extrudate to a residual water content of not more than 10% by weight.

24. In a detergent or cleaning composition, the improvement wherein the composition contains from about 0.1 to about 5% by weight of the enzyme granules produced by the process of claim 23.

* * * * *